(12) United States Patent
Powell et al.

(10) Patent No.: US 7,456,939 B2
(45) Date of Patent: *Nov. 25, 2008

(54) METHOD AND APPARATUS FOR CHEMICAL MONITORING

(75) Inventors: Gary B. Powell, Petaluma, CA (US); Herbert E. Litvak, San Jose, CA (US)

(73) Assignee: Lightwind Corporation, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/428,315

(22) Filed: Jun. 30, 2006

(65) Prior Publication Data

US 2007/0064227 A1     Mar. 22, 2007

Related U.S. Application Data

(63) Continuation of application No. 10/897,314, filed on Jul. 22, 2004, now Pat. No. 7,072,028.

(60) Provisional application No. 60/490,084, filed on Jul. 25, 2003, provisional application No. 60/490,372, filed on Jul. 25, 2003, provisional application No. 60/490,113, filed on Jul. 25, 2003.

(51) Int. Cl.
*G01N 21/73*     (2006.01)
*G01J 3/443*     (2006.01)

(52) U.S. Cl. .................. 356/72; 356/316; 436/16
(58) Field of Classification Search .............. 356/72, 356/316; 438/16
See application file for complete search history.

(56) References Cited

U.S. PATENT DOCUMENTS

| | | | | |
|---|---|---|---|---|
| 5,326,975 | A * | 7/1994 | Barna | 250/372 |
| 6,769,288 | B2 * | 8/2004 | Ward et al. | 73/40.7 |
| 6,975,393 | B2 * | 12/2005 | Mettes | 356/311 |
| 2002/0093652 | A1 | 7/2002 | Powell | |

* cited by examiner

*Primary Examiner*—F. L. Evans
(74) *Attorney, Agent, or Firm*—Ernest J. Beffel, Jr.; Haynes Beffel & Wolfeld LLP

(57) ABSTRACT

The present invention relates to monitoring chemicals in a process chamber using a spectrometer having a plasma generator, based on patterns over time of chemical consumption. The relevant patterns may include a change in consumption, reaching a consumption plateau, absence of consumption, or presence of consumption. In some embodiments, advancing to a next step in forming structures on the workpiece depends on the pattern of consumption meeting a process criteria. In other embodiments, a processing time standard is established, based on analysis of the relevant patterns. Yet other embodiments relate to controlling work on a workpiece, based on analysis of the relevant patterns. The invention may be either a process or a device including logic and resources to carry out a process.

2 Claims, 5 Drawing Sheets

METHOD AND APPARATUS FOR CHEMICAL MONITORING

RELATED APPLICATIONS

This application is a continuation of application Ser. No. 10/897,314 issued as U.S. Pat. No. 7,072,028 on Jul. 4, 2006, which claims the benefit of provisional applications filed on 25 Jul. 2003, Application No. 60/490,084, entitled "Method and Apparatus for Chemical Monitoring of Atomic Layer Deposition (ALD) Processes" by inventor Herbert E. Litvak; Application No. 60/490,372, entitled "Method and Apparatus for Optical Emission Leak Detection in Vacuum Systems" by inventors Herbert E. Litvak and Gary B. Powell; and Application No. 60/490,113, entitled "Method and Apparatus for Monitoring Chemical Utilization/Efficiency in Chemical Processing Equipment" by inventors Herbert E. Litvak and Gary B. Powell, which provisional applications are hereby incorporated by reference.

This application is also related to and incorporates by reference the International Application No. PCT/US01/44585 entitled "Method and Device Utilizing Plasma Source for Real-Time Gas Sampling" filed in the U.S. Receiving Office on 29 Nov. 2001 designating the U.S. and other countries and published in English, which claims the benefit of U.S. application Ser. Nos. 10/038,090 filed by inventors Richard L. Hazard and Gary Powell on 29 Oct. 2001 and 09/726,195 filed by Applicant Lightwind Corporation and inventor Gary Powell on 29 Nov. 2000; and incorporates by reference U.S. application Ser. No. 09/631,271 entitled "Inductively Coupled Plasma Spectrometer for Process Diagnostics and Control" filed by inventor Gary Powell on 2 Aug. 2000. Various patents have issued in this family and continuations are pending.

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

1. Field of the Invention

The present invention relates to monitoring chemicals in a process chamber using a spectrometer having a plasma generator, based on patterns over time of chemical consumption. The relevant patterns may include a change in consumption, reaching a consumption plateau, absence of consumption, or presence of consumption. In some embodiments, advancing to a next step in forming structures on the workpiece depends on the pattern of consumption meeting a process criteria. In other embodiments, a processing time standard is established, based on analysis of the relevant patterns. Yet other embodiments relate to controlling work on a workpiece, based on analysis of the relevant patterns. The invention may be either a process or a device including logic and resources to carry out a process.

2. Description of Related Art

Semiconductor manufacturing has adopted various telemetry techniques utilizing mass spectrometry or spectrographic analysis to improve the cleaning, conditioning or operation of reaction chambers in which a variety of reactions take place, such as deposition, cleaning, etching, implantation, ashing, etc. Telemetry techniques help operators monitor processes that take place on a microscopic level inside a closed chamber that often is sensitive to any form of outside radiation. One technology sometimes used is monitoring a plasma reaction chamber to view radiation emitted by process plasma. Another technology is to use a mass spectrometer to analyze residual gases. More recently, these inventors have begun using a spectrometer having a plasma generator to analyze process gases.

One area of process analysis interest is the efficiency of a chemical reactor and its ability to transform feed gases (which themselves may not be reactive) into reactive species, which can undergo and/or produce desired chemical changes. In a plasma etcher, the action of the plasma may convert stable, otherwise unreactive feed gases into reactive chemical atoms and radicals that then remove surface materials on the substrate to be etched. An example is the plasma breakdown of unreactive CF4 into highly reactive F atoms, which remove Si, SiO2, and/or Si3N4 from the surface of silicon wafers. In plasma-assisted deposition, the plasma may assist in breakdown of a precursor such as TaCl5 into Ta atoms, which are deposited onto a semiconductor surface.

Chemical conversion efficiency, sometimes called "chemical utilization" is rarely measured, because of the difficulty of making proper chemical measurements.

Another area of interest is monitoring of atomic layer deposition (ALD), also known as alternating layer deposition. ALD is a method of depositing thin films of materials onto substrates, including the fabrication of semiconductor electronic devices. As opposed to more conventional deposition methods (e.g. Chemical Vapor Deposition—CVD, or thermal film growth), in which the important steps of film formation (e.g. adsorption of precursor species onto the substrate, followed by chemical reaction steps of the adsorbed film) occur simultaneously, ALD breaks the steps into separate, discrete processing steps, in order to achieve preferred film properties. These properties may include step coverage, across-wafer uniformity, and reduced film contamination. The ALD process can be carried out at lower substrate temperatures than other deposition processes, which is useful generally and, in particular, in temperature-sensitive processes.

A related area of interest is detection of air leaks into a process chamber. One process for leak detection is described in "Air Leak Evaluation of a Production Dry Etcher by Means of Optical Emission Spectroscopy", F. Ciaovacco, S. Alba, F. Somboli, G. Fazio, AEC/APC Symposium XIV, 2002. The technique described requires a plasma in the process chamber to cause emission of light with a wavelength attributed to CN. The CN is formed by chemical combination in the plasma of carbon atoms from a flow of carbon-containing feed gas, e.g. CF4, which has been admitted to the reaction chamber for this purpose and N atoms from N2 molecules in the air leak. The described technique is applied to a plasma reaction chamber, using a window to observe emissions from the plasma. The technique described does not work with non-plasma process chambers where there is no ionization.

Given the anticipated desire for improved process control, a process and related device that addresses any or all of the areas of interest above and/or related areas of interest would be well received. A workable telemetry process would create an opportunity to improve manufacturing process performance.

SUMMARY OF THE INVENTION

The present invention relates to monitoring chemicals in a process chamber using a spectrometer having a plasma generator, based on patterns over time of chemical consumption. The relevant patterns may include a change in consumption, reaching a consumption plateau, absence of consumption, or presence of consumption. In some embodiments, advancing to a next step in forming structures on the workpiece depends on the pattern of consumption meeting a process criteria. In other embodiments, a processing time standard is established, based on analysis of the relevant patterns. Yet other embodiments relate to controlling work on a workpiece, based on analysis of the relevant patterns. The invention may be either a process or a device including logic and resources to carry out a process. Particular aspects of the present invention are described in the claims, specification and drawings.

BRIEF DESCRIPTION OF THE DRAWINGS

A schematic block diagram of a monitoring system is shown in FIG. 1.

Determination of a final steady state value is illustrated by FIGS. 4-5.

DETAILED DESCRIPTION

Figure 1:
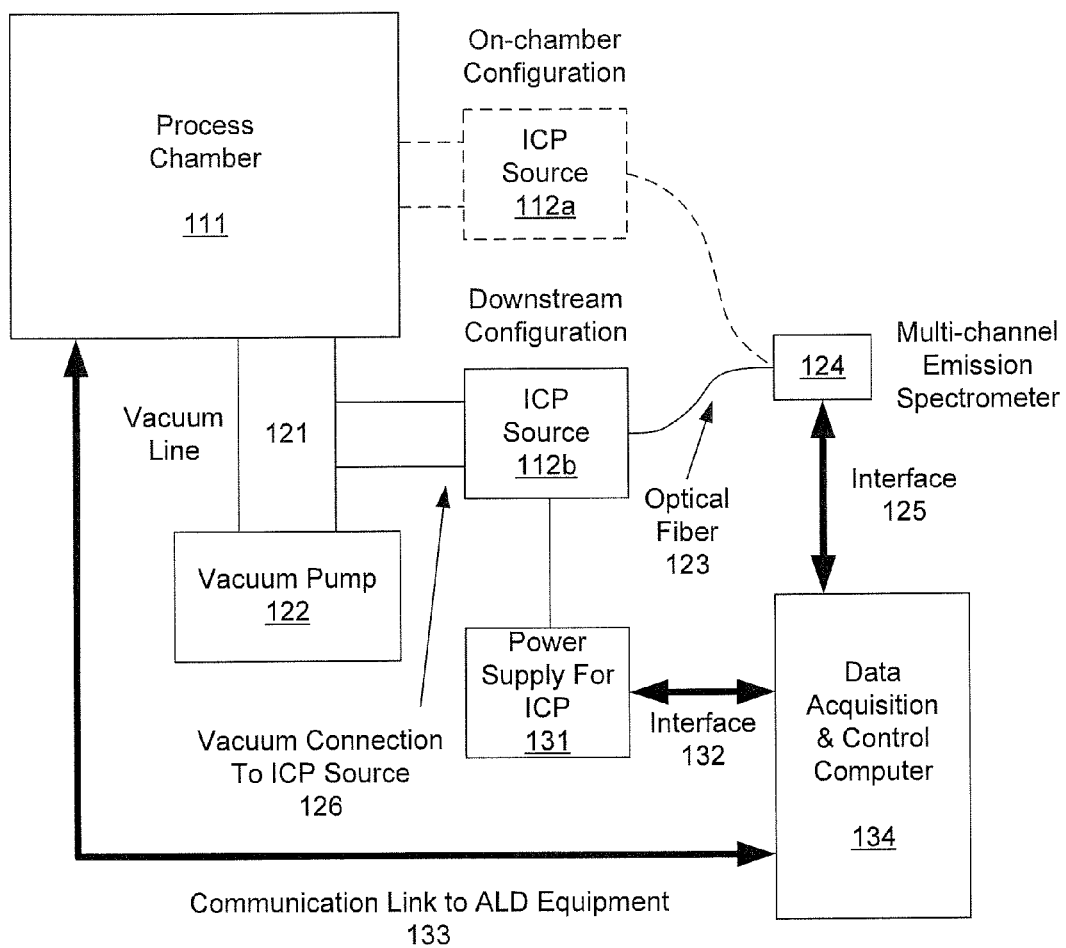

The following detailed description is made with reference to the Figures. Preferred embodiments are described to illustrate the present invention, not to limit its scope, which is defined by the claims. Those of ordinary skill in the art will recognize a variety of equivalent variations on the description that follows.

A variety of spectrometers having a plasma generator may be used with the methods described below. A spectrometer system in this disclosure includes a plasma generator and an array of detectors, such as a spectrometer. An optical detector monitors concentrations of gases in the plasma generator, by means of their plasma-excited characteristic optical emission signals. The plasma generator includes an excitation chamber and external electrodes. The chamber may be made of a variety of materials that are compatible with a range of processes being monitored. Etch reactions typically require corrosive gases and significantly affect excitation chamber material choices. A quartz chamber, for instance, is unlikely to be compatible with etch processes containing fluorine, because quartz is etched by fluorine. Ceramics, such as high purity aluminum oxide (sometimes called alumina) or sapphire, are suitable for monitoring fluorine etch processes. Ceramics having substantial silicon content are less desirable, because fluorine or chlorine can remove the silicon. Boron carbide and nitride are other ceramics that resist fluorine and chlorine and might be used as a structural or coating material. Zirconia is another ceramic that may have the desired characteristics. Generally, any ceramic-like material may be used that is compatible with sustained exposure to fluorine or other halogen-based reactive chemical gases. Preferably, the ceramic-like material should be compatible with both fluorine and chlorine etching.

An excitation chamber preferably has a small volume, such as 40-70 cubic centimeters, as power requirements are low per volume and it is preferred to use a low power level to sustain a plasma discharge. Low power requirements eliminate the need for water or forced air cooling, which may be used in alternate embodiments. Low power requirements tend to extend the lifetime of components. Typical power requirements depend on the process that the system is monitoring. Power levels of 15 to 75 watts are suitable for a wide range of monitoring tasks. Power levels of 50 to 75 watts are suitable for monitoring a higher-pressure process, above 1 torr, such as a stripping process. Power levels of 20 to 50 watts are suitable for monitoring etch and deposition processes. Power levels as low as 5 to 20 watts could be used if the plasma excitation chamber were reduced in size to a volume of approximately 5 to 15 cubic centimeters. A smaller chamber in the volume range of 1 to 5 cubic centimeters could be used although gas transport at pressures below 150 millitorr may reduce its responsiveness. It is desirable for the power setting of an excitation chamber to be software controlled and adjusted, manually or automatically, to modify the light emission from the plasma. The software can evaluate the light emission at a chosen wavelength or set of wavelengths during a chosen stage of operation and adjust the power to generate the desired light emission. Alternatively, recipes can be developed based on experience that includes particular power levels for particular circumstances where the software can automatically step through sequences that match the state or condition of the process operation. The power adjustment impacts the overall instrument sensitivity. This provides a second way to increase system sensitivity to spectral emissions.

The plasma generator can use a range of RF frequencies for excitation. One useful frequency is 13.56 MHz+/−1 MHz, which is an unlicensed operating band. Other frequencies from 1 MHz to 900 MHz are also useful. At the low end of the range, frequencies of 1 MHz or greater require less driving voltage to generate a plasma. At the upper end, the response of the ions and electrons to the excitation frequency changes their behavior. Within the overall range, other frequencies are available while those that do not require licensing are preferable. Use of the predominate 13.56 MHz drive frequency generates a familiar spectral output. Other frequencies that also may be used include 27 and 40 MHz. Excitation frequencies below 1 MHz can cause increased erosion (sputtering) of electrode materials and therefore reduced source lifetimes. Frequencies at or above 1 MHz are more efficiently coupled through dielectrics such as quartz or ceramics. External electrodes can be problematic to implement below 1 MHz with ceramic or anodized aluminum excitation chambers, for instance. A requirement for plasmas powered by external electrodes is efficient power transfer through the dielectric. Many applications use gases that chemically attack source materials or walls. In using materials that are chemically durable, excitation frequencies above 1 MHz couple power more effectively into the plasma. Frequencies above 900 MHz can be harder to ignite. A preferred range of operating frequencies is about 13 to about 40 MHz.

The source can operate from below 5 millitorr to above 5 torr without requiring pressure control or additional pumping while requiring minimal power input.

The window material through which the spectra are transmitted is made of sapphire because of its resistance to most process chemistry. A secondary issue is the deposition of sampled gas byproduct on the sapphire window. When the plasma generator for the spectrometer has the capability of having reducing or other reactive gases added directly to it, those gases may be ionized and act in a manner to keep the spectral transmission window clean. This secondary gas input allows the use of the gases without contamination or effect on the actual process chamber.

A variety of detector arrays can be used with this invention, as described more fully in the disclosures incorporated herein by reference. A useful configuration of detectors and a diffraction grating includes spacing the detectors in relation to the diffracted light so the detectors are responsive to band widths sufficiently narrow that a plurality of detectors are responsive to a single peak in an emission spectrum. A prepackaged device capable of focusing detectors on wave bands of 1.23 nm FWHM bandwidth is a Sony ILX511 device. In an alternative embodiment, a Sony device with a USB interface can be used. Either Sony device includes a 2,048 detector CCD array and a diffraction grating. Individual elements are 12.5 mm×200 mm. The well depth of an individual element at 600 nm is 160,000 photons. The estimated sensitivity may be expressed as 86 photons/count, 2.9×10−17 joule/count, or 2.9×10−17 watts/count for 1-second integration. Its effective range is 200-1000 nm and its integration time may be 3 ms with a 1 MHz A/D card or 4 ms with a 500 kHz A/D card. The Sony IXL511 device can be configured with a grating that diffracts radiation in the 200 to 850 nm spectrum. A slit of 25 mm is typical, with 10, 50 and 100 mm slits available. Various combinations of groove density, fiber diameter and slit width can be selected for additional sensitivity or a wider spectral range. Optics suitable to UV radiation in the 200-350 nm range are used. Order sorting is accomplished with a single-piece, multi-bandpass detector coating for applications in the 200-850 nm spectrum. Detector enhancements that increase UV sensitivity are susceptible to false signals at shorter wavelengths. A coating is used to reduce the effects of wavelengths that are second or third harmonics of the signal of interest. A scan time for collecting and converting data from the array elements is 20 milliseconds or less. In a cost-sensitive application, a more modest array having 1024 or 512 detectors can be used. In an even more cost-sensitive application, a plurality of detectors can be used, either with a diffraction grating or with filters that effectively tune the respective detectors to specific wave bands or wavelengths.

A processor, logic and resources with various capabilities are coupled to the spectrometer. In one embodiment, the logic and resources recognize the start of individual process steps, analyze the relevant optical emission signals from the optical detector in terms of concentrations of chemical species, and optionally communicate this information to a user or the processing tool. This system also could be configured to control the plasma generator, the optical detector, and relevant peripheral components. Suitable interface hardware and software allow the spectrometer with a plasma generator to communicate with a user or the process tool.

A schematic block diagram of a monitoring system is shown in FIG. 1. A process chamber 111 is shown, without the detail of feeds or processes conducted in the chamber. Two different configurations of the plasma generator 112a, 112b are shown in FIG. 1. The solid lines show the configuration 112b for process monitoring downstream of the process chamber. The process chamber is connected to an exhaust or vacuum pump 122 via an exhaust or vacuum line 121. The spectrometer with a plasma generator is branched 126 off the exhaust line and exhaust gas diffuses into the ICP source 112b. This configuration may be advantageous if gas pressures in the process chamber are too high for acceptable operation of the plasma generator. A variation on this configuration, which is not illustrated, flows at least part of the gas through the ICP source, of relying on diffusion. A pressure reducer may be used with this flow through variation. Alternatively, under appropriate pressure conditions, the plasma generator can be mounted directly onto the process chamber, as shown in dashed lines 112a. Chamber gases diffuse into the source. Also illustrated are a power supply 131 for the source 112, a multi-channel emission spectrometer 124, a data acquisition and control computer 134 and various couplings. An optical fiber 123 couples the source 112 with the spectrometer 124. An interface 125 couples the spectrometer 124 with the computer 134. Another interface 132 couples the power supply 131 with the computer 134. A third interface 133, such as a communications link, may couple the tool 111 with the computer 134. This link can include any number of standard communication protocols commonly in use in the semiconductor equipment industry, e.g., analog, digital logic level (TTL), SECS-GEM, TCP/IP, or other.

Chemical Utilization

One application of monitoring chemicals in a process chamber is monitoring of chemical utilization. A process that applies to this and other areas of interest may include monitoring gas in the process chamber with a spectrometer having a plasma generator, calibrating the monitoring, and introducing the first chemical and forming or patterning a layer on a workpiece, while observing a pattern over time of consumption of a first chemical based on the intensity of the spectral peaks. Calibration of the monitoring may include flowing a known quantity or concentration of the first chemical into the process chamber and observing an intensity of one or more spectral peaks of a second chemical, the spectral peaks corresponding to consumption of the first chemical. Generally, calibration may establish run-time process monitoring standards or process time standards, as two ways of applying the results of analysis to process control. Such a process, optionally, also may apply to the layer formed or patterned as a layer of one or more semiconductor device structures. The process further may include advancing to a next step in forming the structures on the workpiece after the pattern of consumption over time of the first chemical meets a process criteria. Various process criteria are described below.

Chemical utilization may focus on current chemical utilization, changing chemical utilization, patterns of utilization or cumulative utilization. Calibration of detector signals in terms of chemical concentrations can be obtained for stable species, by flowing a known concentration of the species of interest (e.g. CF4) into the chemical monitor, and observing the strength of its associated characteristic optical emission signal (e.g. 262 nm CF2 emissions are characteristic of CF4 concentrations). A calibration coefficient can be calculated, e.g., as the ratio of observed signal to known chemical concentration. Alternatively, more sophisticated methods can be employed, such as using several different known species concentrations, and calculating the calibration coefficient as a function, such as a linear slope, of the signal vs. concentration curve.

Figure 2:
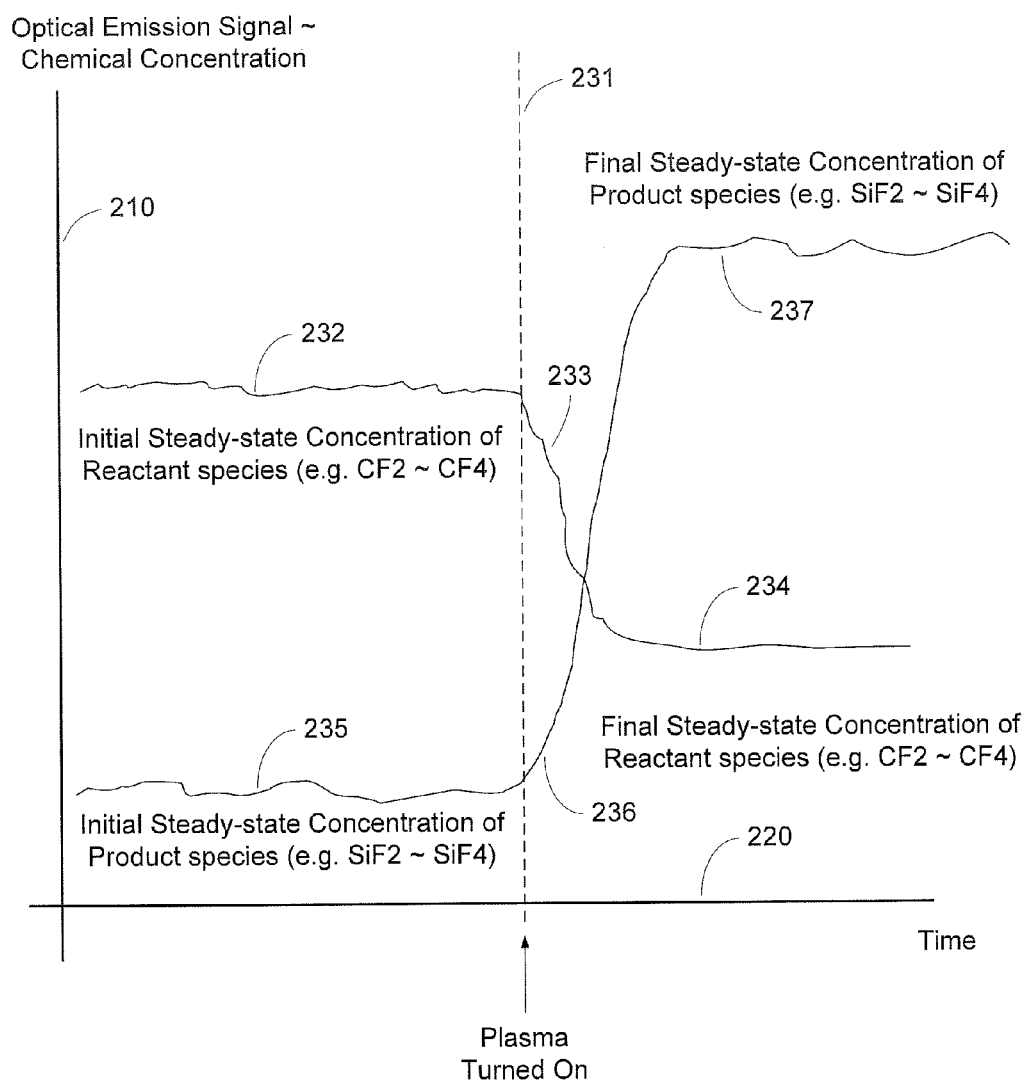
FIG. 2 illustrates one type of signal behavior that can be obtained.

FIG. 2 illustrates one type of signal behavior that can be obtained. In this figure, the optical emission signal strength is plotted on the vertical axis 210. The signal strength may be proportional to chemical concentration. The horizontal axis 220 represents time. Two curves are depicted, 232-233-234 and 235-236-237. A reactant species, such as CF4, is introduced into a process chamber. During a first time interval, to the left of 231, the concentration of the first species is relatively steady, with variations inherent in measurement or in the process. When the stable CF4 is used in an etching process, plasma processing converts it into a reactive species, CF2. A spectrometer with a plasma generator can readily measure emissions from plasma of the reactive species CF2. In a plasma etching chamber, the consumption of CF2 depends on the surface being etched. Removing a patterned resist layer, for instance, may produce a first relatively stable concentration 232 of CF2. As the resist layer is exhausted in patterned areas, for instance exposing silicon, the consumption of CF2 changes, as indicated by the downward slope 233, to the right of 231. Due to variations in resist layer thickness, gas flow, or other reasons, the change in CF2 concentration is not instantaneous. After a time, CF2 begins reacting with the underlying layer producing a second relatively steady pattern of consumption 234. Chemical utilization monitoring can be applied to the initial steady-state concentration 232, the changing concentration that corresponds to a change in the reaction within the process chamber 233 or the second steady-state concentration 234. In parallel with changed CF2 concentration, silicon-fluorine compounds, such as SiF2 and SiF4 change in concentration. Before etching breaks through the resist layer, the initial steady state concentration of silicon reaction products has a relatively low concentration 235. As the consumption of CF4 changes, so does the production of reaction products 236. In a typical case, the production of reaction products reaches a second relatively stable pattern corresponding to consumption of the reactant species being fed into the process chamber.

A simple measure of chemical utilization ("CU") can be calculated from the data of FIG. 2, such as CU=(Final Steady-state CF2 Signal–Initial Steady-state CF2 Signal)/(Initial Steady-state CF2 Signal), or CU=(Final Steady-state SiF2 Signal–Initial Steady-state SiF2 Signal)/(Final Steady-state CF2 Signal—Initial Steady-state CF2 Signal).

Either of these definitions (or several others that can be devised) provides a useful measure of processing tool efficiency, which can be tracked over time and utilized in a statistical (or other) process control scheme. In the case of stable species, e.g. CF4, CU can be calculated in terms of absolute concentrations, provided the required calibration work has been done. For transient species, e.g. F atoms, the calculated CU will be relative, but still extremely useful in a process control scheme. Such a process control scheme can greatly improve reactor productivity and reduce the amount of misprocessed material, by quickly flagging "out of spec" reactor efficiency.

The chemical monitor described here is well adapted to give real-time readouts of chemical concentrations, both before and immediately after plasma turn-on in the chemical reactor, thus providing for calculation of CU in near real time for every wafer passing through the plasma reactor.

An example of implementation on a plasma-processing chamber is shown. This technique is, however, independent of that requirement. Spectrographic characterization can rely on relative peak heights of identified species; however, those same peaks and ratio of peak heights may exhibit a unique behavior with respect to the ionization source used. Comparison of spectra from different process chambers may be limited because of the different ionization properties of those chambers. Among spectrometers, use of a consistent plasma generator reduces the difference in ionization properties. Any semiconductor manufacturing process that has a gas ionization source may be a candidate for the application of this technique.

Other chemical processes, such as thermally enabled deposition also can be characterized by application in this way. For thermally enabled deposition, chemical utilization might be monitored while making changes in the operating temperature of the system. It is understood that changes in operating temperature may also cause changes in any reaction rate and particularly in thermally enabled deposition. A corollary to monitoring the effect of changed operating temperatures is use of chemical utilization to estimate the temperature of a vessel. When a process has been characterized, reaction rate or chemical depletion can be correlated to those variables, such as operating temperature, which affect the reaction rate. In chemical reactions that are not plasma enhanced, the reaction rate is many times thermally driven, so a change in reaction rate corresponds to a change in temperature.

Several variations on chemical vapor deposition are listed by Encyclopedia.TheFreeDictionary.com, which would be known to one of ordinary skill in the art. "Chemical Vapor Deposition (CVD) is a chemical process for depositing thin films of various materials. In a typical CVD process the substrate is exposed to one or more volatile precursors, which react and/or decompose on the substrate surface to produce the desired deposit. Frequently, volatile byproducts are also produced, which are removed by gas flow through the reaction chamber. [¶] CVD is widely used in the semiconductor industry, as part of the semiconductor device fabrication process, to deposit various films including: polycrystalline, amorphous, and epitaxial silicon, SiO2, silicon germanium, tungsten, silicon nitride, silicon oxynitride, titanium nitride, and various high-k dielectrics. [¶] A number of forms of CVD are in wide use and are frequently referenced in the literature."

Metal-Organic CVD (MOCVD) processes use metal-organic precursors, such as Tantalum Ethoxide, Ta(OC2H5)5, to create TaO, Terta Dimethyl amino Titanium (or TDMAT) and, in turn, to create TiN.

Plasma Enhanced CVD (PECVD) processes utilize a plasma to enhance chemical reaction rates of the precursors. PECVD processing allows deposition at lower temperatures, which is often useful in the manufacture of semiconductors.

Remote Plasma Enhanced CVD (RPECVD) is similar to PECVD, except that the wafer substrate is not directly in the plasma discharge region. Removing the wafer from the plasma region allows processing temperatures approaching room temperature.

Rapid Thermal CVD (RTCVD) processes use heating lamps or other methods to rapidly heat the wafer substrate. Heating only the substrate rather than the gas or chamber walls helps reduce unwanted gas phase (gas-to-gas contact) reactions that can lead to particle formation.

Atmospheric Pressure CVD (APCVD) processes proceed at atmospheric pressure.

Low Pressure CVD (LPCVD) processes take place at sub atmospheric pressures. Reduced pressures tend to reduce unwanted gas phase reactions and improve film uniformity across the wafer. Most modern CVD processes are either LPCVD or UHVCVD. Ultra-High Vacuum CVD (UHVCVD) processes proceed at very low pressures, typically in the range of a few to a hundred millitorr.

Atomic Layer CVD (ALCVD) is a process in which two complementary precursors (e.g. Al(CH3)3 and H2O) are alternatively introduced into the reaction chamber. Typically, one of the precursors will adsorb onto the substrate surface in molecular layers, but cannot completely decompose without the second precursor. The precursor adsorbs until it covers the surface and attenuates atomic forces that cause the adsorption. Further progress in layer deposition cannot occur until the second precursor is introduced. Thus, the film thickness is controlled by the number of precursor cycles rather than the deposition time, as is the case for conventional CVD processes. In theory, ALCVD allows for extremely precise control of film thickness and uniformity.

CVD precursor materials fall into a number of categories such as:

- Halides—TiCl4, TaCl5, WF6, etc
- Hydrides—SiH4, GeH4, AlH3(NMe3)2, NH3, etc
- Metal Organic Compounds—
- Metal Alkyls—AlMe3, Ti(CH2tBu)4, etc
- Metal Alkoxides—Ti(OiPr)4, etc
- Metal Dialylamides—Ti(NMe2)4, etc
- Metal Diketonates—Cu(acac)2, etc
- Metal Carbonyls—Ni(CO)4, etc
- Others—include a range of other metal organic compounds, complexes and ligands.

Application of chemical utilization monitoring may permit characterization of various interesting points in production processes. For instance, changed chemical utilization may signal changes in the etch or deposition rate of materials due to different surface areas that etch. Changes in utilization may result from changes in hardware configuration, for instance replacement of materials that react to a greater or lesser extent with the process chemistry. Consumption rates of equipment components that react chemically to the plasma or chemical process (for example, quartz is etched in the presence of fluorine) can be monitored. Build up of materials deposited in a chamber, either deliberately or as reaction byproducts (for example, polymers that contribute to particulate generation) can be monitored.

Atomic Layer Deposition

A typical cycle of ALD steps would include: 1) pumping out or purging the system to remove unwanted or residual gases; 2) admit a precursor gas, such as TaCl5 in the case of Ta deposition, allowing it enough contact time with the substrate to form a monolayer of adsorbed TaCl5; 3) pumping out or purging excess TaCl5; 4) contacting the precursor with a reactive gas, such as atomic H from the dissociation of H2 or NH3, allowing it enough contact time with the adsorbed TaCl5 to react away the Cl atoms (forming gaseous HCl), thus leaving a monolayer of Ta; and 5) pumping out or purging excess H (plus undisassociated H2 or NH3) and the HCl reaction product. In some processes, little or no distinct purging may be required, as the flow of one gas into the process chamber naturally displaces the prior gas.

Since the amount of film deposition in any one ALD process cycle is extremely low (typically <~1A), many cycles (sometimes hundreds or thousands) must be repeated, in order to achieve usable film thickness. Even if a process cycle requires only a few seconds, the necessity of repeating it so many times produces a very slow overall process (~1 hour being typical). Thus wafer throughput may become a hurdle to integrating ALD into a semiconductor device manufacturing flow.

Decreasing overall ALD process time involves decreasing times of individual steps. One may decrease the contact time of the gases with the substrate in steps 2) and 4), above, and/or to reduce the pump out or purge times in steps 1), 3), and 5). Chemical utilization monitoring may be able to detect patterns of adsorption. For example, in step 2), after TaCl5 is introduced, when the TaCl5 concentration reaches a steady-state (or other pre-selected) value, it would be safe to assume that no more adsorption of TaCl5 onto the surface is occurring, and further contact time would have no benefit. Similarly, applied to the chemical reaction in step 4), when the concentration of HCl falls to a steady-state baseline (or other pre-selected) value, it would be safe to conclude that further contact time would have no benefit to film formation, and the process step can be terminated. Similar considerations hold for the pump-out or purge steps: when the concentration of the species to be removed has fallen to a baseline (or other pre-selected) value, there is no point in continuing the purge. Alternatively, when the purge is intended to reduce undesired reactions between gasses, as opposed to gas-to-adsorbed layer reactions, reaction products of gas-to-gas contact could be monitored and patterns of reaction product concentration monitored to determine how short a purge can be applied without excessive gas-to-gas contact reactions. Because so many process cycles are performed in any one deposition, the ability to adjust step times in real-time could have a significant impact on overall process time.

Implemented in a device, logic and resources would be combined with other elements of the spectrometer with a plasma gas source, the logic and resources adapted to recognize the start of the individual process steps, analyze the relevant optical emission signals from the optical detector to recognize "end of process step" signature (e.g. the signal or signal slope achieving a pre-selected value), and communicate this information to a user or the ALD processing tool. A second function of the computer would, optionally, be to control the plasma generator, the optical detector, and relevant peripheral components.

Figure 3:
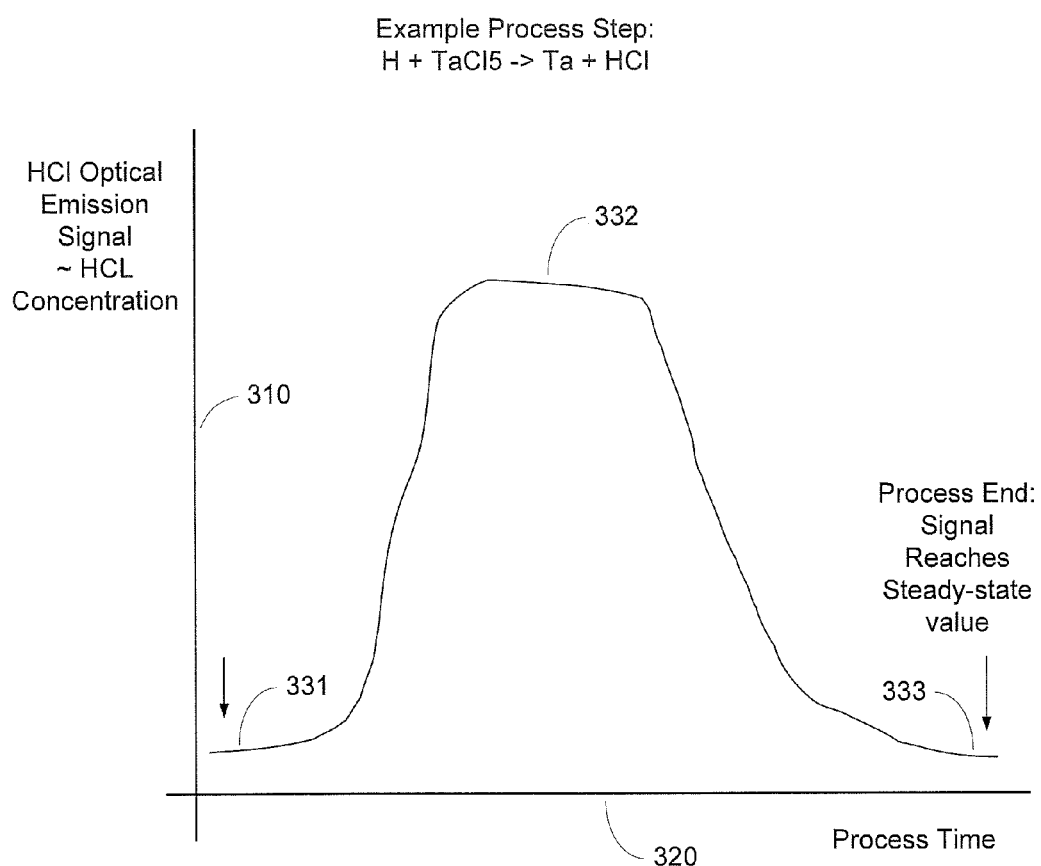
FIG. 3 shows an expected process signal for a TaCl5 and H precursor ALD process.

FIG. 3 shows an expected process signal for the TaCl5 and H ALD process described above. The vertical axis 310 represents the HCL optical omissions signal, which is proportional to HCL concentration. The horizontal axis 320 tracks time. After adsorption of TaCl5, H is introduced into the process chamber. Prior to or at the beginning of the reaction between the precursors 331, the HCL signal is relatively low, following a first steady pattern. Between the process start 331 and the high point of HCL concentration 332, the HCL signal strength trends upward. The reaction proceeds, producing to a relatively steady concentration pattern 332. Then, the HCL concentration drops to a final steady state value 333, which indicates that all of the absorbed TaCl5 has reacted with H, so there is no more Cl to liberate and combine with H. Process termination would be signaled when the HCl signal reaches a steady-state value (indicating cessation of evolution of HCl from the process step).

Figure 4:
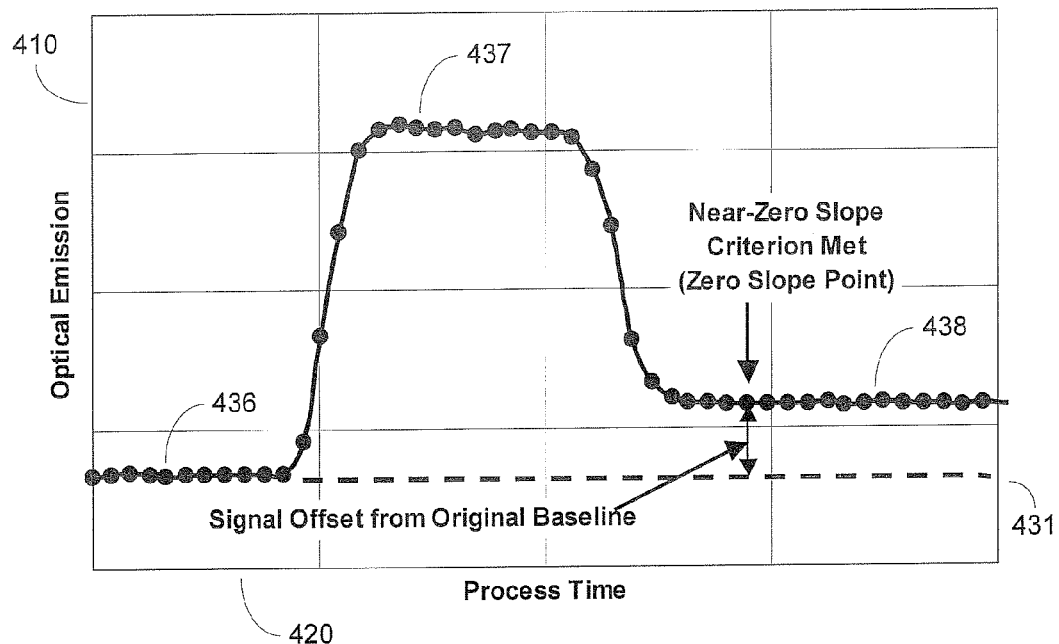
FIG. 4 is a generalized representation of an optical emission signal from an ALD process step, similar to FIG. 3.
Figure 5:
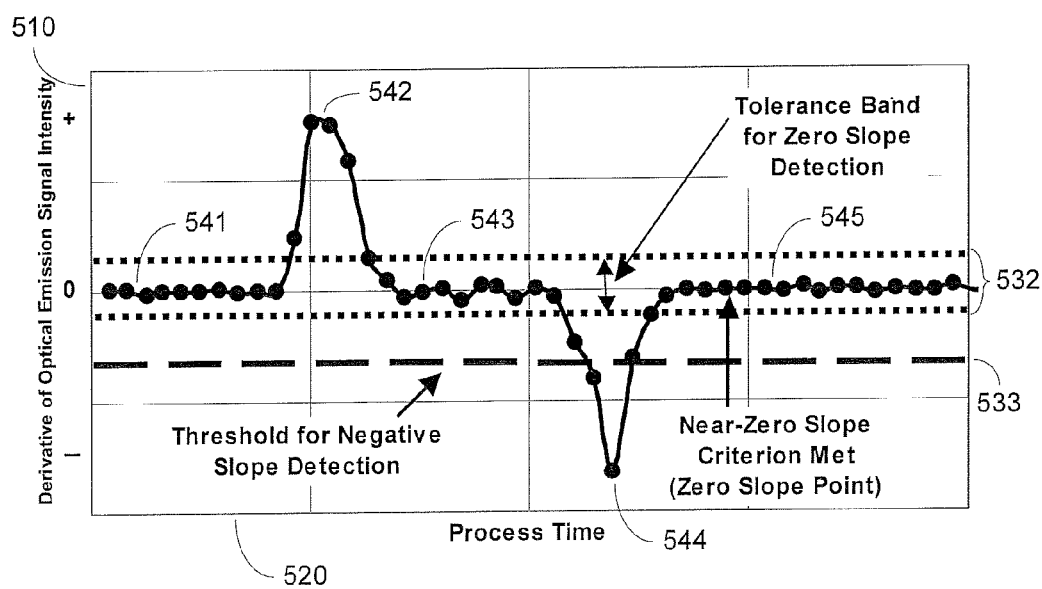
FIG. 5 represents the mathematical first derivative of FIG. 4.

Determination of a final steady state value 333 is illustrated by FIGS. 4-5. FIG. 4 is a generalized representation of an optical emission signal from an ALD process step, similar to FIG. 3. FIG. 5 represents the mathematical first derivative of FIG. 4. Steady-state behavior of chemical concentration in an ALD process step implies that the concentration of the species of interest is no longer changing. Since optical emission signals are proportional to chemical concentrations, steady-state behavior can be inferred from an optical emission signal from the appropriate chemical species that is no longer changing. This is illustrated by FIG. 4. The vertical axis 410 indicates optical emissions signal intensity. The horizontal axis 420 tracks time. A baseline 431 provides a background reference. A signal 436-437-438 changes over time. During a first time interval 436, for instance before H begins reacting with adsorbed TaCl5, the signal is at a baseline. As in FIG. 3, the signal, for instance HCL emissions, rises to a plateau 437, and then drops. A final steady state concentration of HCl 438 is detected, which is expected to be above the original baseline. This final steady state concentration may be flat or slowly diminishing.

Mathematically, it follows that the first derivative of the optical emission signal (i.e. the signal slope) is zero for some period of time (i.e. not simply instantaneously). Thus, steady-state behavior can be inferred by examination of the first derivative of the optical emission signal shown in FIG. 5, for a persistent zero slope or a near-zero slope, taking into account noise sources. In FIG. 5, the vertical axis 510 is a positive or negative value indicating the first derivative of the signal in FIG. 4. That is, a near-zero value of the first derivative 541, 543, 545 corresponds to a flat segment of the signal 436, 437, 438. A positive value of the first derivative 542 corresponds to a rising portion of the signal, as between 436 and 437. A negative value 544 corresponds to a descending portion of the signal, as between 437 and 438. In this figure, a tolerance band 532 is indicated for detecting a near-zero slope. A threshold for negative slope detection 533 also is indicated.

To avoid confusing the steady-state signal behavior at the start of the process step with the desired steady-state behavior at the end of the process step, a mathematical criterion can be imposed, such as a persistent, short-term negative first derivative be detected (e.g., lasting for at least some number k data points, k typically being ~2-10 data points over some time that depends on the sampling rate) before a zero or near-zero first derivative is recognized. This condition is indicated as "Threshold for Negative Slope Detection" in FIG. 3b. The condition can only be met for signals that are decreasing in intensity, i.e. nearing the end of a process step similar to the one in FIG. 3a. Once the "Negative Slope Criterion" has been met, a persistent near-zero slope is a satisfactory indication of a steady-state condition. This "Near-Zero Slope Criterion" can be expressed mathematically as a persistent first derivative signal within a Tolerance Band, as illustrated in FIG. 3b. The persistence can be expressed mathematically as n consecutive first derivative data points (n typically ~2-10), whose value lies within the Tolerance Band (assuming the "Negative Slope Criterion" has already been met.)

Described stepwise, detection of steady-state behavior may include:

1) Acquiring optical emission data points.
2) Calculating the mathematical first derivative of that data point (requires that at least two data points have been acquired).
3) Examining the first derivative relative to the "Negative Slope Criterion" (NSC).
4) If the NSC has not been met, repeat from 1).
5) If the NSC has been met, acquire a new data point, calculate the first derivative, and test if the "Near-Zero Slope Criterion" (NZSC) has been met.
6) If the NZSC has been met, signal "Stop Process" (or similar output) to the ALD processing tool.
7) If the NZSC has not been met, repeat from 5).

An additional mathematical criterion can be imposed on the data at the point that the "Near-Zero Slope Criterion" has been met (="Zero Slope Point"), viz. to compare the optical emission signal at that point with the original baseline signal level of the data (calculated, e.g., as the average of several data points just before or just after the start of the process step). If the former is appreciably above the later, this may indicate an accumulation of some impurity or contaminant in the process chamber, and steps may need to be taken to correct the situation. A suitable warning signal could be displayed on a user interface screen and/or communicated to the ALD process tool over the communication link.

Precursor Sufficiency

As described above, precursors may be combined to form a useful layer on a substrate, as part of a structure of the semiconductor device. In addition, precursors may be combined to form a useful etchant, for instance by adsorption of water vapor followed by introduction of fluorine gas. In some processes, there are many points of potential failure in delivery of precursors to the process chamber. The potential failure points depend on how the precursor is delivered. Three typical modes of delivering precursors are: (a) bubbling a carrier gas through a liquid precursor; (b) atomizing a liquid precursor; or (c) heating and vaporizing a precursor, either from a solid or liquid form. To evaluate the sufficiency of precursor concentrations or quantities in the chamber, an optical emission line of interest can be selected, typically corresponding to one of the decomposition products of converting the precursor to a plasma in the plasma generator. The spectrometer with plasma generator is calibrated using a controlled concentration or quantity of the precursor in the reaction chamber, under conditions simulating the desired process. When the process operates, the spectrometer with plasma generator can compare an optical emission signal to the calibrated standard signal. An operator or the process tool can be advised if too little precursor has reached the process chamber. In some processes, the sufficiency of the precursor in the process chamber can be evaluated before the reaction proceeds, either before energizing a plasma or before introducing an additional precursor. In other processes, many layers accumulate, allowing an opportunity for intervention before the layer is spoiled.

Leak Detection

The method for detection of leaks and other vacuum system contaminants includes several general steps that may be combined or sub combined in various ways. These steps could be performed manually or automatically in a leak detection sequence. The sequence could be started by a maintenance operator, an engineer or by an appropriate message over a communications link from the vacuum system (as part of its internal maintenance procedures). Following is the sequence of events.

1. Determine that the vacuum system is in the desired condition. That condition could be an idle or not processing state. It could also be during an inactive process step when there is gas flow but no ionization of gasses in the process chamber. Initiation of a test of system vacuum integrity could be manual or automatic, by a message from the host system or detection of a particular operating mode. Preferably, the test occurs when there is a determination that the vacuum system has reached a steady-state condition, indicated by constant or relatively steady output of optical emission signals. The vacuum system should be in a mode in which gas pressure and flows are in steady state, such as "processing", "idle", etc. when the leak detection steps are executed. Unsteady gas pressure or flows would complicate leak rate quantification.

2. Acquire emission spectra from the ICP source at wavelengths indicative of an air leak (e.g. 387 nm for CN, a reaction product of leaky nitrogen and a carbon source. These signals constitute "Background" signal levels, SBkg(1).

3. Admit a controlled amount of leak detection gas (e.g., CF4 or SF6), and once again acquire emission spectral signals S(1) from the ICP source at wavelengths indicative of an air leak. By leak detection gas, we mean a gas that reacts with a leak when ionized. This leak detection gas can be introduced to the process chamber or downstream, for instance in the vacuum line 121 (see FIG. 1) or in a vacuum connection 126 between the vacuum line and the plasma generator. Calculate the signal differences, Snet(1)=S(1)−SBkg(1).

4. Open a first calibrated leak, wait for the system to equilibrate, again acquire emission spectral signals S(1), and compute signal differences Snet(1) with the first calibrated leak open.

5. Repeat with one or more additional calibrated leaks in the system.

6. Close calibrated leaks and stop flow of the leak detection gas into the vacuum system.

Figure 6:
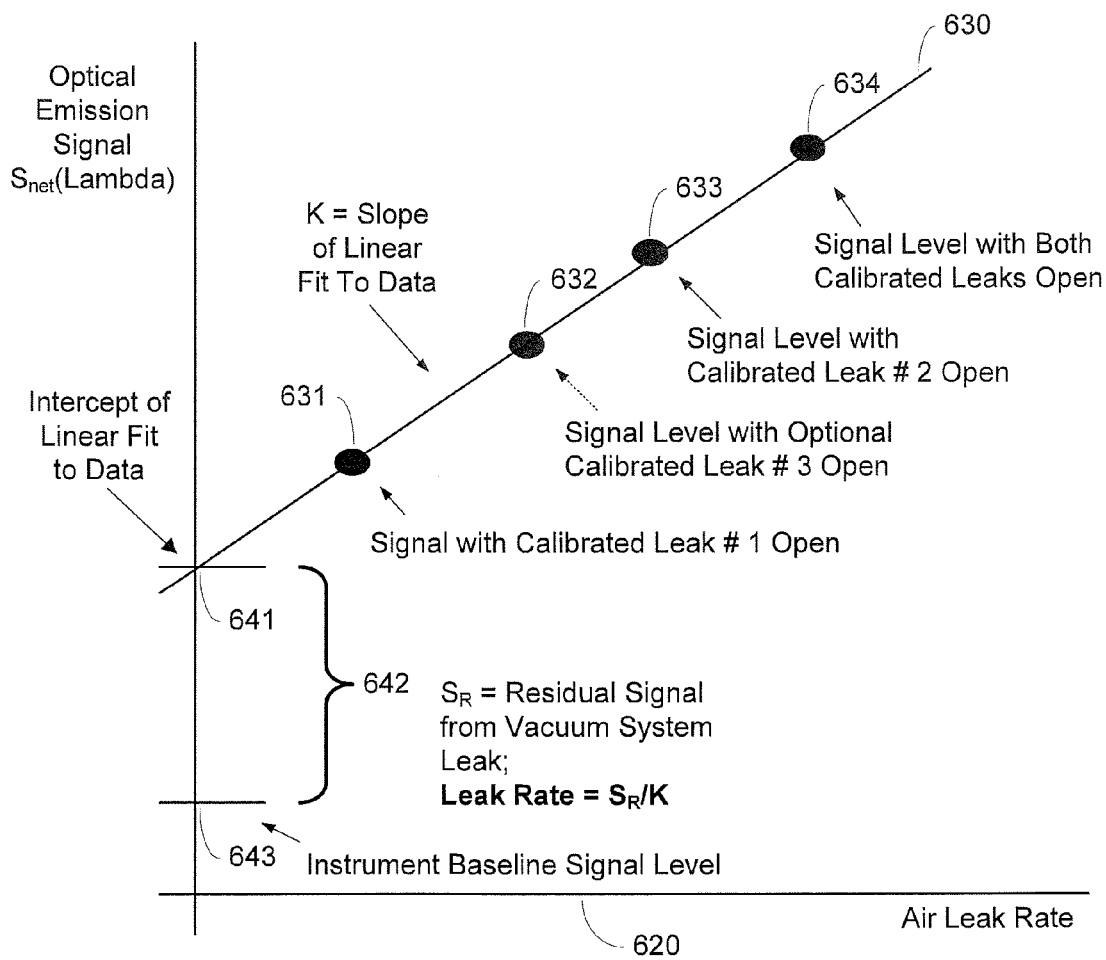
FIG. 6 indicates how the system leak rate can be obtained by comparison of signals with and without calibrated leaks open.

7. Compute system air leak rate. FIG. 6 indicates how the system leak rate can be obtained by comparison of signals with and without the calibrated leaks open. In this figure, the vertical axis 610 is the optical emission signal. The horizontal axis 620 corresponds to a leak rate. A regression line 630 is calculated to correlate the optical omissions signal with the leak rate. It is anticipated that a linear fit will result. At point 631, a signal is recorded corresponding to a first calibrated leak. At point 633, a signal level is recorded corresponding to a second calibrated leak. Optionally, at point 634, a signal level is recorded with both first and second calibrated leaks. As a further option, additional points, such as point 632 can be recorded, corresponding to additional calibrated leaks. From the regression line 630, an intercept 641 can be calculated. At some intercept value, a residual vacuum system leak is apparent, because the intercept value is above 642 a baseline optical omissions signal 643 for a system with no leaks. This baseline signal may be calculated, for instance, with the plasma generator not energized, to take into account stray current and other factors impacting the spectrometer.

If signals from multiple wavelengths 1 are obtained, a separate leak rate can be calculated for each wavelength utilized. Standard statistical methods can then be used to calculate a "best estimate" leak rate. Another approach would be to calculate a signal-to-noise ratio (SNR) at each of the wavelengths being tracked, and use only the wavelengths of highest SNR for leak rate determination. (This latter method builds in protection against unanticipated spectral interferences that may arise in the vacuum system.)

8. Report computed leak rate to a user at the computer monitor and to the vacuum system. Optionally, the computed leak rate can be compared to one or more tolerance values, to determine suitability of the system for further operation. "System OK", "System Warning" or "System Abort" signals can optionally be sent to the vacuum system based upon comparison of the computed leak rate with tolerance values.

9. Signal "Procedure End" state to the vacuum system.

While this calibration process has been described in the context of leak detection, the same process for correlation of particular flows through the process chamber with optical emission signals at the spectrometer with plasma generator can be applied generally, either with or without regression through the data points.

We have observed that optical leak detection can also be detected by attenuation of certain chemical signals (e.g. F atom emission at 703.7 nm from leak detection gases such as SF6), in addition to the formation of new signals (e.g. CN.) When SF6 is used as a leak detection gas, a leak attenuates a signal associated with the SF6. Thus the signal Snet(1) may be a negative number. This attenuation mode may be more sensitive for leak detection in some environments than formation of a new signal.

Use of the downstream source allows leak detection to be performed in a non-plasma system or under conditions when the etch plasma is not active, e.g. during equipment "maintenance" or "idle" states, and in systems which do not have plasma generation capability, or the ability to optically monitor a plasma. Thus, leak detection can be performed virtually any time the system is under vacuum, not just when etching is being performed. In addition, leak detection may be more sensitive (e.g. have a lower detection limit) when the system is in idle or maintenance mode than in etch mode, because of spectral interferences from etch reactant or product gases during etch. Using this approach, baseline gas breakdown and energy levels can be characterized and used as references.

Real time or near real time processes can be compared to this reference and changes in the process that generate byproduct or consume reactant can be compared to the reference. Because emission spectra can be correlated to concentration changes, reaction rates/depletion rates can also calculated as they occur.

Additional Embodiments

The present invention may be practiced as a method or device adapted to practice the method. In one environment, the methods disclosed are used to form structures of semiconductor devices on the surface of a wafer. The methods disclosed also can be used to form a layer on a workpiece, such as a layer that is part of a structure of a semiconductor device on a wafer. The invention can be viewed from the perspectives of manufacturing a device, of operating manufacturing equipment, of controlling a manufacturing process, or of responding to gaseous inputs with analytical or control information. Software that embodies aspects of the invention may be an article of manufacture, such as media impressed with logic to carry out any of the disclosed methods. Also as an article of manufacture, software that embodies aspects of the invention may be practiced as the data stream carrying logic adapted to carry out the disclosed methods.

A first method embodiment provides a method of monitoring chemical utilization within a process chamber. This method includes monitoring gas in the process chamber with a spectrometer having a plasma generator that is gaseously coupled to the process chamber. The gaseous coupling may be directly to the process chamber, as through a port, or to an exhaust from the process chamber. The gaseous coupling may operate by diffusion into or by gaseous flow through the plasma generator. Types of process chambers that are mentioned in some detail above include plasma etching, non-plasma dry etching, and many types of deposition chambers. Other reaction chambers to which the disclosed methods might be applied include cleaning, implantation and ashing chambers. Application of the methods disclosed is not meant to be limited to these types of semiconductor manufacturing process chambers, or to semiconductor manufacturing. The method further includes calibrating the monitoring by flowing a known quantity or concentration of the first chemical into the process chamber and observing an intensity of one or more spectral peaks of the second chemical, the spectral peaks corresponding to consumption of the first chemical. The first chemical may be consumed by decomposition or by reaction with other chemicals. Typically, multiple detectors of narrow bandwidth will fit under the spectral peaks of the second chemical. With experience, these inventors have learned, contrary to their prior teachings, that stoichiometric analysis using a known, nonreactive gas, such as argon, is not necessary in order to calibrate a spectrometer having a plasma generator. Even across machines, it now appears that standards can be established using a spectrometer having a plasma generator based on standard process chamber operating conditions, without undue experimentation. This method embodiment further includes introducing the first chemical and forming or patterning a layer on a workpiece, while observing a pattern over time of consumption of the first chemical based on the intensity of the spectral peaks. The first chemical may be introduced to the reaction chamber, between the reaction chamber and the plasma generator or, in the case of leak detection, outside the reaction chamber. Introducing the first chemical and forming or patterning a layer on a workpiece may proceed simultaneously or in sequence. In most processes, the intensity the spectral peaks will be observed while forming or patterning the layer. In some processes, for instance, for leak detection or precursor sufficiency evaluation, the spectral peaks may be observed and evaluated prior to forming or patterning the layer, so as to avoid spoiling a workpiece or as to allow correction of or compensation for a problem. A pattern over time of consumption is observed, rather than just an instantaneous spectral intensity. Over time, the dynamics of the process can be monitored. Rates of processes and changes in rates of processes can be observed. Monitoring can be applied to one or more gases flowing through the chamber at a predetermined rate or it can be applied to one or more gases dumped into the chamber in a predetermined quantity or concentration. That is, a continuous flow, plug flow or batch reactor design can be monitored.

An additional, optional aspect of this method takes into account that the layer formed or patterned in the introducing step described above is a layer of one or more semiconductor device structures on the workpiece. This aspect further includes advancing to the next step in forming the structures on the workpiece after a pattern of consumption over time of the first chemical meets a process criteria. The process criteria depends on how the method is being applied, for instance to chemical monitoring, atomic layer deposition or leak detection.

One process criteria is a cumulative amount of the first chemical consumed over time.

Another process criteria applies to a precursor that mixes with one or more other gases. This process criteria is that a sufficient amount of the precursor is present in the gas mixture to form the layer. The pattern of consumption over time may begin before the precursor is introduced and may reflect adsorption of the precursor onto the workpiece. In this instance, the precursor will be consumed in the plasma generator of the spectrometer, by decomposition. Alternatively, the pattern of consumption over time may follow adsorption of another precursor onto the workpiece, so the consumption involves combining two precursors. In a reaction chamber with ionizing energy, for instance, this process criteria may be evaluated prior to energizing a plasma in the process chamber.

Two further process criteria look at a changing rate of consumption corresponding to a change in one or more reactions in the process chamber. One looks for an indication that the consumption rate has begun to change and the other looks for an indication that the consumption rate has changed and stabilized. In terms of a curve, the first looks for curve segment that is relatively steady or flat followed by a curve segment that rises or falls. The second looks for a curve segment that is rising or falling, followed by a curve segment that is relatively steady or flat. In some instances, the process criteria may involve a first relatively steady pattern of consumption, followed by a changing rate of consumption, followed by a second steady rate of consumption.

Several process criteria may be applied to leak detection. One leak detection criteria uses the first chemical that is a leak detection gas that reacts with a leak gas in the plasma generator to produce the second chemical. Applying this process criteria, the calibrating step of the first method embodiment further includes flowing a calibrated leak gas into the process chamber. The process criteria for advancing to a next step in forming structures of the device is substantial absence of the leak gas. Details of calibration and analysis for one embodiment are given above. Optionally, introducing the first chemical precedes the forming or patterning step and observing consumption over time coincides with introducing the first chemical. For some processes, the leak detection process criteria may be evaluated prior to energizing a plasma in the processing chamber.

Several aspects of the first leak detection criteria optionally may be applied. The leak detection gas may be a carbon-fluorine compound, such as $CF_4$. It may be a sulfur-fluorine compound, such as $SF_6$.

The second leak detection criteria uses the first chemical that is a leak detection gas, introduced between the process chamber at the plasma generator that reacts with a leak gas in the plasma generator to produce the second chemical. Applying the second detection criteria avoids any need to introduce the leak detection gas into the process chamber. Like the first leak detection criteria, applying this criteria, the calibrating step further includes flowing a calibrated leak gas into the plasma generator and the process criteria is substantial absence of the leak gas. Again, this process criteria may be evaluated prior to energizing a plasma in the process chamber that is used for the forming or patterning.

The third leak detection criteria uses a first chemical that is a leak tracing gas, that is, a chemical that leaks into the process. This first chemical reacts with other gases to produce the second chemical. For instance, a leak tracing gas that includes a carbon compound may reacts with nitrogen that also leaks into the chamber or which is ambient and the chamber to produce a carbon-nitrogen compound such as CN. The leak tracing gas should be a material that is substantially lacking from the ambient atmosphere surrounding the process chamber, which is introduced to the ambient atmosphere surrounding the process chamber to locate one or more leaks. This method may pinpoint a leak into a chamber operating at a sub atmospheric pressure.

Another approach to chemical monitoring and process criteria is using the chemical monitoring to set a process criteria, which is a production time standard; that is, to set a standard time interval during which a production step proceeds. One way of setting a process criteria, according to this approach, includes applying the introducing and forming or patterning step one or more times to test workpieces and establishing a production time standard for the forming or patterning of the layer, based on a cumulative amount of the first chemical consumed over time. It further includes forming or patterning a layer of one or more structures on a production workpiece using the production time standard, wherein the process criteria for advancing to the next step is the production time standard. This production time standard approach recognizes that the staff of a fabrication facility will be familiar and comfortable with production recipes that include production time standards for various production steps. An experienced and credible staff unit may use consumption monitoring to set production time standards that are then applied in the manufacturing of structures and semiconductor devices.

A second way of setting a process criteria, according to this approach, includes applying the introducing and forming or patterning step one or more times to test workpieces and establishing a production time standard for the forming or patterning of the layer, based on a changing rate of consumption for the first chemical corresponding to a reaction in the process chamber after a relatively steady pattern of consumption. It further includes forming or patterning a layer of one or more structures on a production workpiece using the production time standard wherein the process criteria for advancing to the next step is the production time standard.

Another way of setting a process criteria includes applying the introducing and forming or patterning step one or more times to test workpieces and establishing a production time standard for the forming or patterning of the layer, based on a second relatively steady pattern of consumption of the first chemical, which follows both a first relatively steady pattern of consumption and a changing rate of consumption that corresponds to a reaction change in the process chamber. It further includes forming or patterning a layer of one or more structures on a production workpiece using the production time standard, wherein the process criteria for advancing to the next step is the production time standard.

Several alternative aspects and features of the first method embodiment do not depend on advancing to a next step in forming the structures on the workpiece after the pattern of consumption over time meets a process criteria. The several alternative aspects and features that follow will sound familiar, but they depend directly from the first method embodiment identified above.

According to one aspect of the first method embodiment, the gas coupling between the process chamber and the spectrometer having a plasma generator includes directing exhaust gas from an exhaust of the process chamber to the plasma generator. According to an alternative aspect, the gaseous coupling includes diffusion from a port on the process chamber into the plasma generator.

Coordinated with observing the pattern of consumption over time, the method further may include controlling work on the workpiece based on a cumulative amount of the first chemical consumed over time. Or, it may further include, when the first chemical is a precursor that mixes with one or more gases, controlling work on the workpiece based on a sufficient amount of precursor in the gas mixture for forming or patterning the layer. When the first chemical is a precursor, the sufficiency of the precursor may be evaluated prior to energizing a plasma in the process chamber that is used for the forming or patterning.

Coordinated with observing the pattern of consumption over time, the method alternatively may further include controlling work on the workpiece based on a consumption rate curve. The consumption rate curve may indicate a changing rate of consumption of the first chemical corresponding to a change in one or more reactions in the process chamber, after a relatively steady rate of consumption. The consumption rate curve may indicate a relatively steady rate of consumption of the first chemical, and after a changing rate of consumption corresponding to a change in one or more reactions in the process chamber. Or, the consumption rate curve may indicate a second relatively steady pattern of consumption of the first chemical, after a first relatively steady pattern of consumption followed by a changing rate of consumption corresponding to change in one or more reactions.

For leak detection, coordinated with observing the pattern of consumption over time, one option uses the first chemical that is a leak detection gas that reacts with the leak gas in the plasma generator to produce the second chemical. Following this option, the calibrating step further includes flowing a calibrated leak gas into the process chamber and the method further includes controlling work on the workpiece based on a substantial absence of the leak gas. One aspect of this option may involve introducing the first chemical before the forming or patterning and the 5 observing over time is coincident with introducing the first chemical. Another aspect is that the substantial absence of leak gas may be evaluated prior to energizing a plasma in the process chamber that is used for forming or patterning.

An alternative option for leak detection introduces the first chemical that is a leak detection gas between the process chamber and the plasma generator.

A different option for leak detection uses the first chemical that is a leak tracing gas. Following this option, the leak tracing gas reacts with other gases to produce the second chemical and controlling work on the workpiece is based on a substantial absence of the leak tracing gas. The leak tracing gas may be a material substantially lacking from an ambient atmosphere surrounding the process chamber, which is introduced to the ambient atmosphere surrounding the process chamber to locate one or more leaks.

Production time standards may be set depending directly from the first method embodiment. The general approach involves applying the introducing and forming or patterning step one or more times to test workpieces and establishing a production time standard, then forming or patterning a layer of one or more structures on a production workpiece using the production time standard. There are at least three options for setting the production time standard. One is basing the standard on a cumulative amount of the first chemical consumed over time. Another is basing the standard on a changing rate of consumption of the first chemical corresponding to a reaction change in the process chamber, after a relatively steady pattern of consumption. The third is basing the standard on a second relatively steady pattern of consumption of the first chemical, and after a first relatively steady pattern of consumption followed by a changing rate of consumption of the first chemical corresponding to changing reaction.

While the embodiments above generally include either proceeding to the next step in forming a device or controlling work on the workpiece, the methods disclosed may usefully be practiced without either proceeding to the next step or controlling work.

Several additional embodiments are described in the provisional applications identified above and incorporated by reference. A further method embodiment is a method of detecting a steady chemical condition within a process chamber. This method includes introducing a chemical mixture into the process chamber and monitoring the chemical mixture in a device outside the process chamber, utilizing a spectrometer with plasma generator, and detecting at least one emission signal. This embodiment further includes observing the detected emission signal and detecting that at least one component of the chemical mixture was being consumed by reaction and observing the detected initial signal and detecting that the consumption of the component was substantially reduced.

Another method embodiment of detecting a steady chemical condition within a process chamber includes introducing a chemical mixture into the process chamber and monitoring the chemical mixture in a device outside the process chamber, utilizing a spectrometer having a plasma generator and detecting at least one emission signal. This embodiment further includes observing the detected emission signal and detecting that a rate of consumption of a component of the chemical mixture has consequently changed.

Several more leak detection embodiments can be described. One begins with a process chamber in an initial state and includes monitoring a gas composition in a device outside the process chamber, utilizing a spectrometer having a plasma generator and detecting at least one emission signal "A". This embodiment further includes providing a monitor gas that is reactive with a leak gas and detecting at least one emission signal "B". It further includes introducing a calibrated leak gas into the process chamber and detecting at least one emission signal "C". The emission signals "A", "B" and "C" are then used to calculate a leak rate of infiltration of the leak gas into the process chamber. One option for this embodiment is introducing the calibrated leak gas to the reaction chamber through at least two leak ports. Another aspect is that at least two of the emission signals use the same optical emission wavelengths.

Another leak detection embodiment is a method of detecting a leak into a process chamber, the process chamber beginning in an initial state. This embodiment includes monitoring a gas composition in a device outside the process chamber, utilizing a spectrometer having a plasma generator. It further includes providing a monitor substance positioned in the device outside the process chamber that is reactive with the leak gas and detecting at least one initial emission signal. The monitor substance may be a gas or a solid, such as a block of carbon or activated charcoal. It may be placed in or near the plasma generator. This embodiment further includes introducing a calibrated leak gas into the process chamber and detecting at least one calibrated emission signal and calculating a rate of infiltration of the leak gas into the process chamber using the initial and calibrated emission signals. One option for this embodiment is introducing the calibrated leak gas to the reaction chamber through at least two leak ports.

Another leak detection embodiment is a method of detecting a leak into a process chamber, the process chamber beginning in an initial state. This embodiment includes providing a device outside the process chamber, utilizing a spectrometer having a plasma generator and a monitor substance that is reactive with leak gas. It further includes establishing a baseline emission signal with the process chamber in an acceptable state and monitoring a gas composition in the device outside the process chamber to detect a change in the baseline emission signal produced by reaction of the monitor substance with the leak gas. One option for this embodiment is that the change from the baseline may be detected prior to energizing a plasma in the process chamber.

One chemical utilization embodiment includes introducing a consumable chemical into the process chamber and monitoring the consumable chemical in a device outside the process chamber, utilizing a spectrometer having a plasma generator and detecting at least one ignition signal. This embodiment further includes observing the detected emission signal and detecting at least one proxy for the consumed chemical. It further includes integrating over time consumption of the consumed chemical.

A second chemical utilization embodiment, like the first, includes introducing a consumable chemical into the process chamber and monitoring the consumable chemical in a device outside the process chamber, utilizing a spectrometer having a plasma generator and detecting at least one emission signal. Unlike the first, it includes observing the detected emission signal and detecting that a rate of consumption of at least one proxy for the chemical mixture has changed.

A monitor device embodiment includes a plasma generator external to and gaseously coupled to the process chamber, a spectrometer including detectors optically coupled to a plasma generator, and a device electronically coupled to the spectrometer including detectors, the device including logic and resources adapted to carry out any of the methods described above, including embodiments, aspects, options and features of those methods in various combinations.

While the present invention is disclosed by reference to the preferred embodiments and examples detailed above, it is understood that these examples are intended in an illustrative rather than in a limiting sense. It is contemplated that modifications and combinations will readily occur to those skilled in the art, which modifications and combinations will be within the spirit of the invention and the scope of the following claims.

We claim as follows:

1. A method of monitoring a process chamber for leaks, including:
   monitoring gas in the process chamber with a spectrometer having a plasma generator that is gaseously coupled to the process chamber;
   introducing a leak detection substance in a location downstream of the reaction chamber, wherein the leak detection substance is reactive with a suspected leak gas; and
   forming or patterning a layer on a workpiece, while observing with the spectrometer a pattern over time of one or more spectral peaks corresponding to reaction of the leak detection substance with the suspected leak gas.

2. The method of claim 1, wherein the layer formed or patterned is a layer of one or more semiconductor device structures.

* * * * *